(12) United States Patent
Bellqvist et al.

(10) Patent No.: US 9,290,372 B2
(45) Date of Patent: Mar. 22, 2016

(54) FLUID DISTRIBUTOR UNIT

(75) Inventors: Peter Bellqvist, Uppsala (SE); Klaus Gebauer, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/703,382

(22) PCT Filed: Jun. 14, 2011

(86) PCT No.: PCT/SE2011/050727
§ 371 (c)(1),
(2), (4) Date: Dec. 11, 2012

(87) PCT Pub. No.: WO2011/159232
PCT Pub. Date: Dec. 22, 2011

(65) Prior Publication Data
US 2013/0087246 A1    Apr. 11, 2013

(30) Foreign Application Priority Data
Jun. 15, 2010    (SE) ..................... 1050612

(51) Int. Cl.
*B67D 7/02* (2010.01)
*G01N 30/60* (2006.01)
*B01D 15/14* (2006.01)

(52) U.S. Cl.
CPC .............. *B67D 7/02* (2013.01); *G01N 30/603* (2013.01); *G01N 30/6017* (2013.01); *B01D 15/14* (2013.01); *G01N 30/6026* (2013.01)

(58) Field of Classification Search
CPC ............ G01N 30/6017; G01N 30/603; G01N 30/6026; B67D 7/02; B01D 15/14

USPC ....................... 210/656, 198.2, 456
See application file for complete search history.

(56) References Cited

U.S. PATENT DOCUMENTS

| | | | |
|---|---|---|---|
| 3,334,514 A | | 8/1967 | Catravas |
| 3,879,127 A | * | 4/1975 | Storr et al. ............... 356/36 |
| 4,399,032 A | * | 8/1983 | Mott ..................... 210/198.2 |
| 4,469,597 A | | 9/1984 | Mott |
| 4,557,830 A | * | 12/1985 | Onitsuka et al. ........ 210/198.2 |
| 4,582,608 A | | 4/1986 | Ritacco |
| 4,732,687 A | * | 3/1988 | Muller et al. ............ 210/656 |
| 4,797,209 A | | 1/1989 | Jackson |
| 4,894,152 A | * | 1/1990 | Colvin et al. .......... 210/198.2 |
| 4,968,421 A | * | 11/1990 | Spacek et al. .......... 210/198.2 |
| 5,013,433 A | * | 5/1991 | Shalon ................... 210/198.2 |
| 5,137,628 A | * | 8/1992 | Hart et al. .............. 210/198.2 |
| 5,338,448 A | * | 8/1994 | Gjerde ................... 210/198.2 |
| 5,557,945 A | * | 9/1996 | Mangyo et al. ............ 62/474 |
| 5,985,140 A | * | 11/1999 | Dewaele ................ 210/198.2 |

(Continued)

FOREIGN PATENT DOCUMENTS

| | | |
|---|---|---|
| GB | 2440244 | 1/2008 |
| JP | 2002-214214 | 7/2002 |

(Continued)

*Primary Examiner* — Ernest G Therkorn
(74) *Attorney, Agent, or Firm* — Parks Wood LLC

(57) ABSTRACT

A fluid distributor for uniformly distributing flow of a feed onto a chromatography column in a cost-effective way defines a distribution channel of generally conical shape between a solid back plate and a packed bed in the column, wherein the fluid distributor comprises at least two circular and/or annular fluid-permeable porous disks essentially filling the volume of the distribution channel.

20 Claims, 6 Drawing Sheets

(56) References Cited

U.S. PATENT DOCUMENTS

| | | | |
|---|---|---|---|
| 6,576,124 B2 * | 6/2003 | Pichl et al. | 210/198.2 |
| 6,905,595 B2 * | 6/2005 | Gebauer | 210/198.2 |
| 6,936,166 B1 * | 8/2005 | Salven et al. | 210/198.2 |
| 7,051,758 B2 * | 5/2006 | Bellqvist et al. | 137/561 A |
| 7,399,410 B2 | 7/2008 | Izzo et al. | |
| 7,588,683 B2 * | 9/2009 | Willis et al. | 210/198.2 |
| 2005/0236312 A1 * | 10/2005 | Gebauer | 210/198.2 |
| 2006/0124551 A1 * | 6/2006 | Gjerde et al. | 210/656 |
| 2007/0102358 A1 | 5/2007 | Good | |
| 2011/0094953 A1 * | 4/2011 | Doehren et al. | 210/198.2 |
| 2012/0018381 A1 * | 1/2012 | Gjerde et al. | 210/656 |

FOREIGN PATENT DOCUMENTS

| | | | |
|---|---|---|---|
| JP | 2007-127433 | | 5/2007 |
| JP | 2007-256226 | | 10/2007 |
| WO | WO 99/62609 | | 12/1999 |
| WO | WO 00/50144 | * | 8/2000 |
| WO | WO 03/005018 | | 1/2003 |
| WO | WO 2008/142160 | | 11/2008 |

* cited by examiner

FLUID DISTRIBUTOR UNIT

CROSS-REFERENCE TO RELATED APPLICATIONS

This application is a filing under 35 U.S.C. 371 of international application number PCT/SE2011/050727, filed Jun. 14, 2011, published on Dec. 22, 2011 as WO 2011/159232, which claims priority to application number 1050612-9 filed in Sweden on Jun. 15, 2010.

TECHNICAL FIELD OF THE INVENTION

The present invention relates to a distributor for uniformly distributing a fluid flow onto a porous bed in a column. More specifically it relates to a fluid distributor for a chromatography column.

BACKGROUND OF THE INVENTION

In liquid chromatography and adsorptive separation in general, the fluid distribution system is of paramount importance to the overall performance, particularly for columns with large cross-sections in relation to bed height.

Columns for liquid chromatography normally comprise a vessel filled with a porous bed through which a liquid flows, with separation taking place by material distribution between the liquid and the solid phase of the porous bed. The porous bed is commonly a packed bed, typically formed by consolidating a suspension of discrete particles, but it can also be a monolithic porous body or a stack of porous sheets (membranes). The column often has a cylindrical geometry, with flow passing axially from one end to the other, but columns with radial flow are also well known and non-cylindrical geometries have been described. In all these constructions, the liquid flow must be well distributed from a feed tube over the entire bed surface. As the scaling parameter of chromatography columns is usually the column diameter, with the bed height kept constant, the difficulty of distribution is considerably higher for large-scale columns with correspondingly low height-to-diameter ratios.

A uniform flow distribution is essential in order to obtain good efficiency for the column. Uniform flow distribution is a prerequisite for achieving uniform residence time for all fluid elements passing the packed bed and column, respectively. Any deviations from uniformity will show up as premature breakthrough, low plate numbers or peak asymmetry as they generate an unfavourable broadening in the residence time distribution over the column. Two features of a distribution system are essential for achieving uniform flow distribution: The first feature is the ability of the distribution system to transfer fluid from essentially a single tubing feeding liquid to the column onto the surface of the packed bed such that all fluid elements are applied simultaneously over the packed bed surface. The same simultaneous withdrawal and collection of fluid applies to the removal of fluid at the column outlet. The second critical feature is the ability to maintain uniform pressure across the surface of the packed bed which is yielding a uniform fluid velocity over the bed and the column.

A classical fluid distribution system for axial columns simply consists of a central inlet for the mobile phase in combination with a thin distribution channel (gap) of constant height behind a retainer filter (woven net or sinter) confining the inlet end of the bed. This type of system will by necessity deteriorate strongly in performance with increasing diameter of the column. This is due to the residence time difference between fluid elements travelling from the inlet to the outer column wall and those fluid elements which directly can enter the retainer net and the bed region below the inlet port. Further, the required fluid transfer of liquid throughout the distribution channel towards the column wall will result in a pressure drop across the distribution channel. As a result, the pressure drop over the packed bed and thus the uniformity of the fluid velocity field will be affected.

A better fluid distribution will be provided with a conically shaped flow channel with the largest channel height at the position of highest fluid velocity to balance the volumetric flow in the path. Such conical flow channels have been described in e.g. U.S. Pat. No. 5,137,628 as an open channel below one or two nets or in U.S. Pat. No. 6,936,166 as a pattern of channels in a ribbed plate below a retainer net and a perforated plate. The ribbed plate has the disadvantage of high production cost and complicated design engineering. In the open channel case, there is a high risk for bulging of the retainer net when it is subjected to a) hydrodynamic forces during operation that are counteracting the pressure loss over the porous bed and b) forces from the mechanical compression of the packed bed as result of the packing process and the weight of the bed. Any such bulging will affect the performance of the column negatively. This adverse effect on the column performance is due to volumetric changes of the packed bed geometry as a result of the bulging. These volumetric changes will cause instability as well as inhomogeneous compression and porosity in the packed bed structure. Further, bulging of the retainer net will have an adverse effect on the column performance by reducing and altering the overall volume and dimensions of the distribution channel, hereby leading to changes in fluid velocity and pressure loss along the distribution channel that can strongly deteriorate the overall residence time distribution and performance of the column.

In many cases it is desirable to use only plastic materials in the distributor. This applies both to columns for use with liquids that will corrode stainless steel and to lower cost columns intended for single or short-term use. Plastics have a lower elastic modulus than steel, which puts higher demands on the retainer net support arrangements in order to prevent bulging. It will also be more important to keep manufacturing costs low in the plastics case when a column and distributor design is needed for producing single-use columns and distribution systems that are to be disposed of after a process run or a campaign.

There is thus a need for a low cost distributor giving uniform flow distribution and no retainer net bulging during operation of the column.

SUMMARY OF THE INVENTION

One aspect of the invention is to provide a uniformly distributed flow of a feed onto a chromatography column in a cost-effective way. This is achieved with a fluid distributor as defined in claim 1.

One advantage with such a fluid distributor is that it provides high flow uniformity and is easy to manufacture from readily available materials.

Further suitable embodiments of the invention are described in the depending claims.

DEFINITIONS

The term "generally conical" herein means a three-dimensional shape that tapers smoothly and/or in steps from a larger circular or non-circular base area to a smaller area or point. The base area may be flat or can alternatively be of generally conical shape. Examples of generally conical shapes include truncated and non-truncated circular cones, paraboloids, hyperboloids etc, as well as staircase approximations to these shapes such as a staircase approximation of a cone or truncated cone.

DETAILED DESCRIPTION OF EMBODIMENTS

Figure 1:
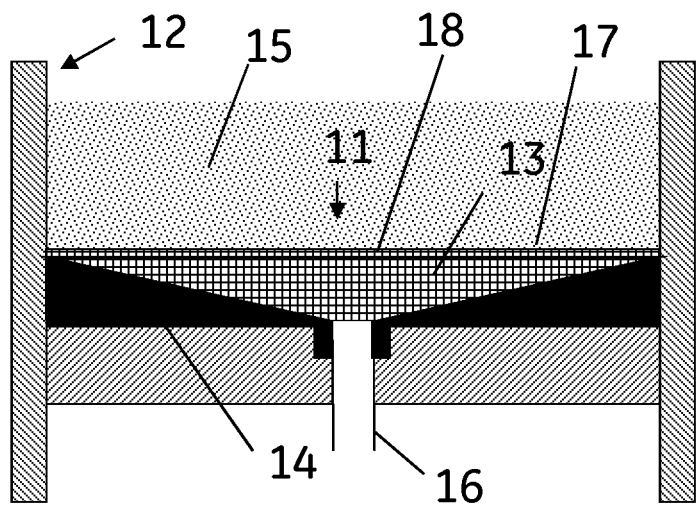
FIG. 1 shows part of a column with a fluid distributor according to one embodiment of the invention.

In one aspect illustrated by FIG. 1, the present invention discloses a fluid distributor 11 for a column 12, defining a distribution channel 13 of generally conical shape between a solid back plate 14 and a packed bed 15 in the column 12, wherein said fluid distributor 11 comprises at least two circular and/or annular fluid-permeable porous disks (not individually shown) essentially filling the volume of said distribution channel 13. One of these porous disks can be a retainer disk 18 in direct contact with the packed bed 15, to prevent migration of particles from the packed bed. Suitably, all the porous disks are arranged to provide unimpeded fluid flow through the disk assembly, i.e. with no barriers between the disks or on the surfaces of the disks. The fluid distributor can be placed in the bottom end of the column 12 with the base area 17 upwards, facing the packed bed 15 and with an inlet/outlet tube 16 downwards. The fluid distributor can also be placed in the top end of the column 12 with the base area 17 downwards, facing the packed bed 15 and with the inlet/outlet tube 16 upwards. Suitably, one fluid distributor is placed in the bottom end of the column and one in the top end and the fluid can move either downwards or upwards through the column. An advantage of having the porous disks essentially filling the distribution channel volume is that retainer disk or retainer net bulging is efficiently prevented, even for low modulus plastic materials, while the pore volume and pore structure allow for uniform distribution of the fluid through the porous disks. One advantage of having at least two porous disks is that it is easier to fill the volume of the distribution channel with disks of easily manufactured simple shapes. Another advantage is that disks of different pore sizes, pore structures and/or materials can be combined to improve the function of the fluid distributor. The fluid permeability of the porous disks can be achieved by having an open pore structure in all the disks, as opposed to e.g. closed cell foams etc which are not permeable to fluids. In one embodiment the disks, such as all the disks, have a three-dimensionally connected pore structure, i.e. they are permeable to fluid both in the axial and in the radial direction. This has the advantage that the entire pore volume of the disks is available for radial distribution of the fluid. The retainer disk 18 may have a three-dimensionally connected pore structure but it can also have a parallel pore structure, in particular if the retainer disk is very thin and sufficient radial distribution is provided by the distributor disks.

Figure 10:
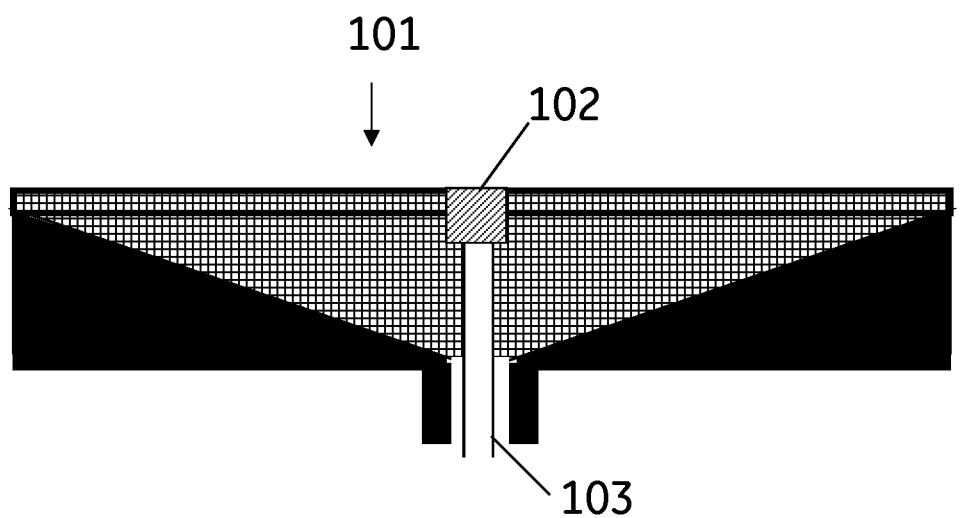
FIG. 10 shows a fluid distributor with a packing/unpacking nozzle according to one embodiment of the invention.

In one embodiment, illustrated by FIG. 10, the fluid distributor 101 comprises a nozzle 102 for packing and unpacking of the column via a packing/unpacking tube 103. This nozzle may be placed centrally in direct contact with the packed bed and to accommodate for it, one or more central fluid-permeable porous disk or disks may have an annular shape—e.g. with a central hole for the nozzle. With the nozzle it is possible to pack and unpack the bed without disassembly of the column, which is a cumbersome procedure.

In one embodiment the total envelope volume of the circular and/or annular fluid-permeable porous disks fills at least 90%, such as at least 95 or 99%, of the distribution channel volume. One advantage of this is that retainer disk or retainer net bulging is prevented. Another advantage is that channelling between the porous disks is minimized or completely prevented.

In one embodiment the diameter of the fluid distributor is at least 20 cm, such as above 40 cm. Uniform flow distribution is more difficult to obtain in larger columns and the fluid distributor of the invention is particularly suited for large scale columns, intended to be used in e.g. bioprocessing, such as separation of proteins or other biopharmaceuticals.

Figure 2:
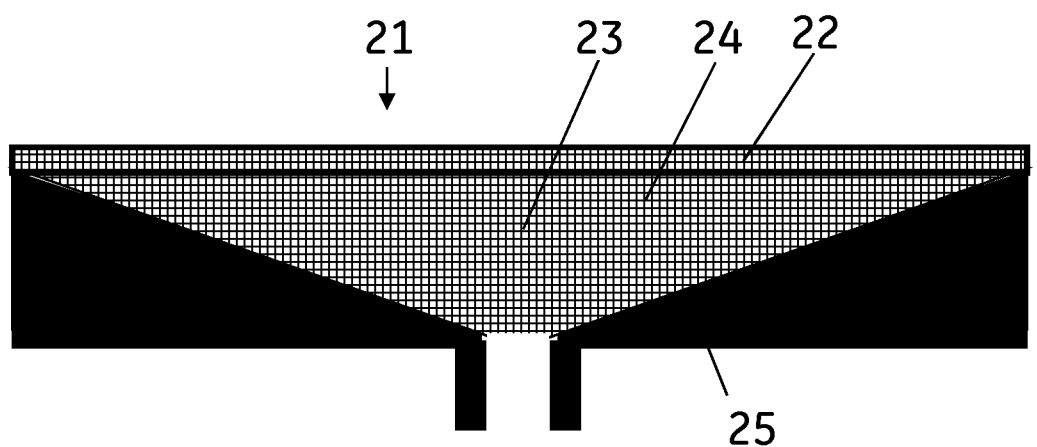
FIG. 2 shows a fluid distributor according to one embodiment of the invention.

In one embodiment illustrated by FIG. 2, the fluid distributor 21 comprises at least two circular and/or annular fluid-permeable porous disks, one of which is a porous retainer disk 22 directly facing the packed bed. At least one circular and/or annular fluid-permeable porous distributor disk 23 fills the part of the distribution channel volume 24 between the porous retainer disk 22 and the solid back plate 25. The porous retainer disk 22 can have a pore size adapted to prevent any migration of particles from the packed bed into the distribution channel, such as having an average pore size smaller than the number average particle size of the packing material. It can have a pore structure suitable for retaining the particles, such as a sintered particle structure, a woven or nonwoven textile structure or a porous membrane structure. It may also be thin, such as below 5 or 3 mm thickness and the flexibility caused by the low thickness is not an issue, as it is well supported by the porous distributor disk/disks. The porous distributor disk/disks 23 can have a pore size and pore structure suitable for distributing the fluid uniformly, such as a pore size in the 0.05-2 mm range and e.g. a sintered particle structure or an open cell rigid foam structure. In one embodiment the fluid distributor comprises at least two, such as at least three or more porous distributor disks 23. In a further embodiment each porous distributor disk 23 has a three-dimensionally connected pore structure, to allow for simultaneous axial and radial flow of the fluid through the distributor.

Figure 3:
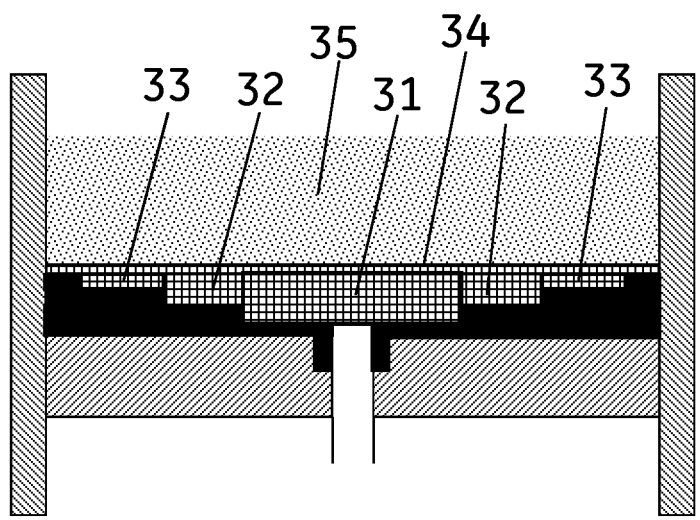
FIG. 3 shows part of a column with a fluid distributor according to one embodiment of the invention.
Figure 4:
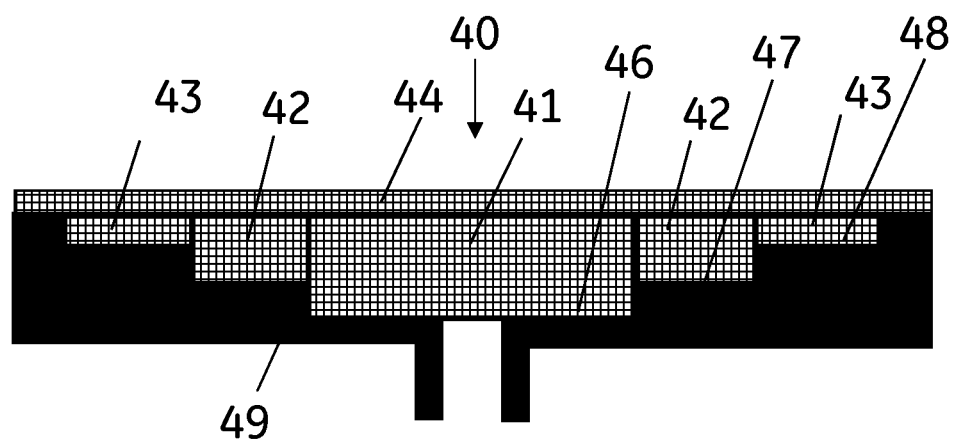
FIG. 4 shows a fluid distributor according to one embodiment of the invention.

In one embodiment, illustrated by FIGS. 3 and 4, a first circular or annular fluid-permeable porous disk 31,41 is concentrically fitted inside a second annular fluid-permeable porous disk 32,42. An advantage of this is that a tight fit can be obtained between the disks. In a specific embodiment said first and second porous disks are planar. An advantage of this is that planar sheets are readily available and only need to be cut into the right shape. Large chromatography columns are made in many diameters with very short series for each diameter and it can be advantageous not to need the investment in specific tooling for preparing disks of non-planar shape. In another embodiment said second porous disk 32,42 has a lower thickness than said first porous disk 31,41. An advantage of this is that the combination of an inner thicker disk and an outer thinner disk fits a generally conical distribution channel. In one embodiment said second annular porous disk 32,42 is concentrically fitted inside a third annular fluid-permeable porous disk 33,43. The third annular porous disk 33,43 can have a thickness lower than the second annular porous disk to fit a generally conical distribution channel. Even a fourth and a fifth annular porous disk may be fitted outside the third annular porous disk. The concentrically fitted disk assembly may be used together with a porous retainer disk 34, 44 covering the whole area directly facing the packed bed 35.

Figure 5:
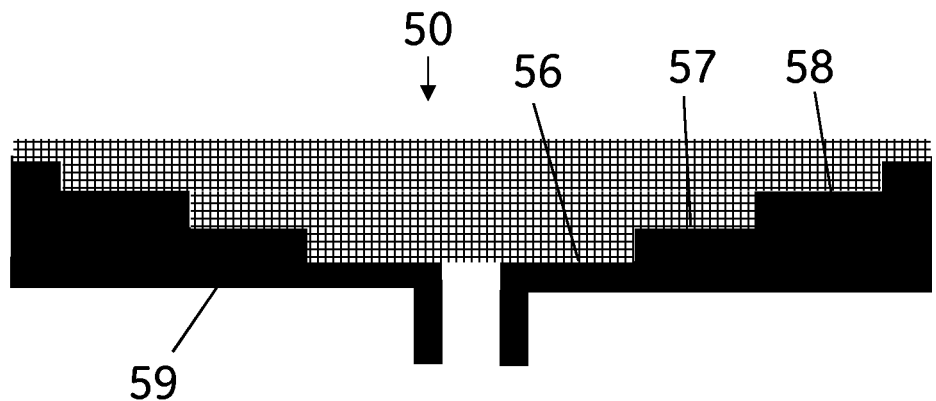
FIG. 5 shows a fluid distributor according to one embodiment of the invention.
Figure 6:
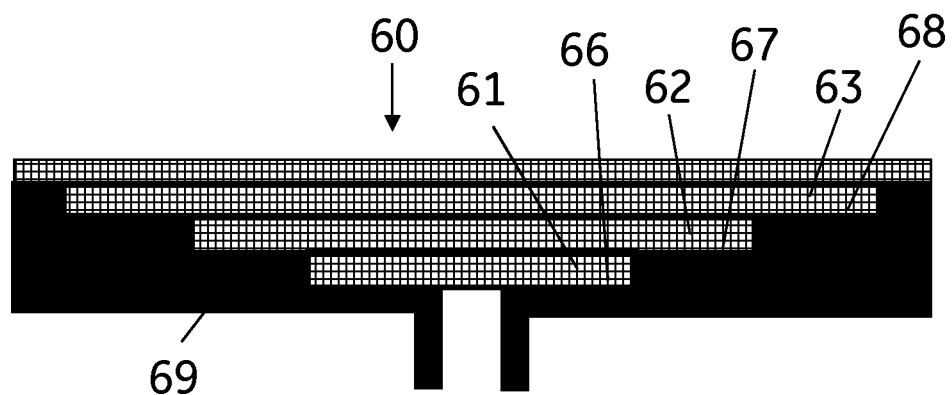
FIG. 6 shows a fluid distributor according to one embodiment of the invention.

In one embodiment, illustrated by FIGS. 4, 5 and 6, the fluid distributor 40,50,60 comprises a circular solid back plate 49,59,69 with a staircase pattern of at least two, such as at least three, four or five internal concentric annular recesses 46-48, 56-58, 66-68 and at least two, such as at least three, four or five circular and/or annular fluid-permeable porous disks 41-43,61-63 (not individually shown in FIG. 5) mounted in said annular recesses. An advantage of this is that a generally conical shape can be essentially filled with a robust assembly of planar disks. In one embodiment, illustrated by FIG. 4, a first circular or annular porous disk 41 is mounted in an inner annular recess 46 and a second annular porous disk 42 is mounted in an outer annular recess 47 and concentrically fitted outside said first circular or annular porous disk 41. In a specific embodiment said second annular porous disk 42 has a lower thickness than said first circular or annular porous disk 41.

In one embodiment, illustrated by FIG. 6, a first circular or annular fluid-permeable porous disk 61 is mounted in an inner annular recess 66 and a second circular or annular fluid-permeable porous disk 62 is mounted in an outer annular recess 67 in planar abutment with said first circular or annular porous disk 61. A third circular or annular fluid-permeable porous disk 63 can be mounted in a further outer annular recess 68 in planar abutment with said second circular or annular porous disk 62. Even a fourth and a fifth porous disk may be mounted in outer recesses. In one embodiment the disks are planar and form a stack. An advantage of this is that if the fit between the disks is not tight, the interstitial space will be in a direction perpendicular to the column axis and will not cause any channelling effects. Another advantage is that easily available sheets of standard thicknesses can be used to make a stack of the desired thickness. Suitably, the disks are mounted in annular recesses on a solid back plate 79.

Figure 7:
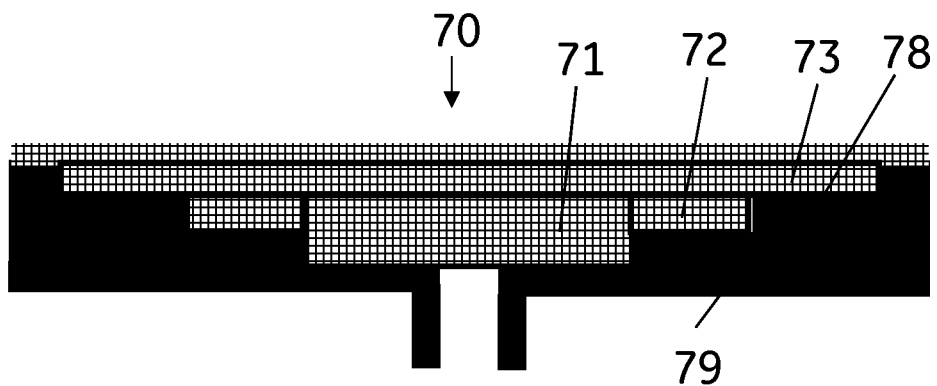
FIG. 7 shows a fluid distributor according to one embodiment of the invention.

In one embodiment, illustrated by FIG. 7, the fluid distributor 70 comprises a first circular or annular fluid-permeable porous disk 71 concentrically fitted inside a second annular fluid-permeable porous disk 72 and a third annular fluid-permeable porous disk 73 mounted in an annular recess 78 in planar abutment with one or both of said first and second porous disks 71,72. Further fluid-permeable porous disks may also be fitted, either concentrically outside disks 72 or 73 or in planar abutment with disk 73 or any further disk. An advantage of this is that it can be possible to make a better approximation to a conical shape with a limited number of available sheet thicknesses.

Figure 8:
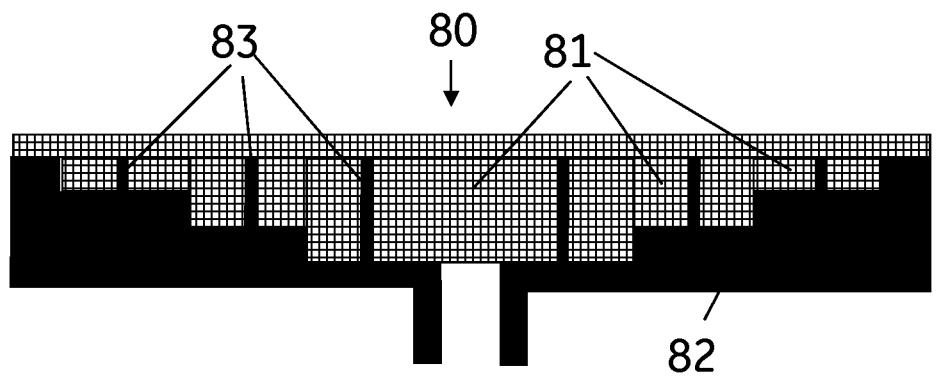
FIG. 8 shows a fluid distributor according to one embodiment of the invention.
Figure 9:
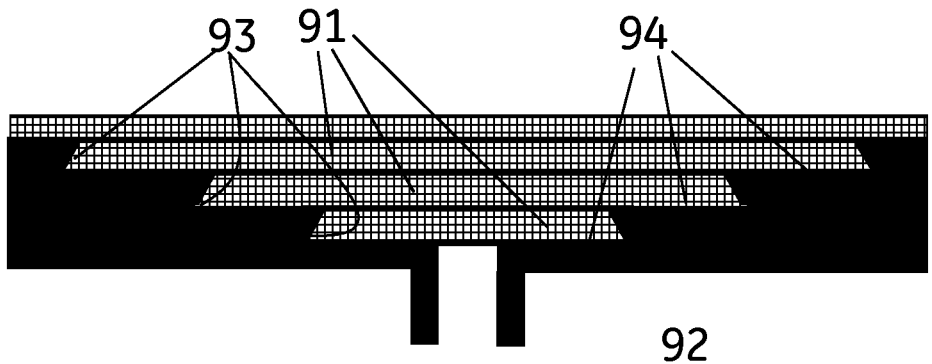
FIG. 9 shows a fluid distributor according to one embodiment of the invention.

In one embodiment, illustrated by FIGS. 8 and 9, at least one of the porous disks 81,91, such as at least two, three or even all the porous disks are fixed to the solid back plate 82,92. The disks can be welded, e.g point welded together and to the solid back plate. They can also be fixed with other fixture elements, such as being snap fit elements, screws and other elements known in the art. In one specific embodiment of the fluid distributor 80, illustrated by FIG. 8, the porous disks 81 and the solid back plate 82 are manufactured from the same type of polymer and welded together. The welds may be point welds 83 going through several disks. In another embodiment illustrated by FIG. 9 the edges 93 of the annular recesses 94 on the solid back plate 92 form an acute angle with the plane of each recess. An advantage of this is that the recess edges can be used as snap fits for the edges of the porous disks.

Figure 11:
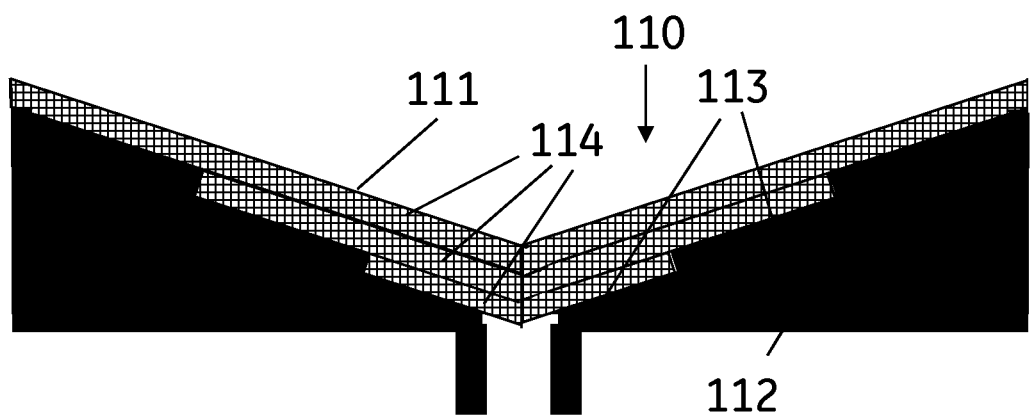
FIG. 11 shows a fluid distributor according to one embodiment of the invention.

In one embodiment, illustrated by FIG. 11, the base area 111 of the distribution channel in the fluid distributor 110 is of generally conical shape. This shape can be selected to modulate the nominal height of the packed bed as function of radius with the purpose of optimising the overall residence time distribution over the column for specific applications. This bed height modulation typically requires the application of a very small and precise angle at said generally conical shape of the base area. In this configuration, it is of outmost importance to avoid any bulging of the retainer net or disk as this would have a strong negative effect on the column function. One way to achieve a base area 111 of generally conical shape is to have a solid base plate 112 with angled recesses 113 and annular or circular porous disks 114 shaped to fit into the recesses 113, e.g. by heat forming.

In one embodiment at least one of the porous disks, such as each porous disk, comprises a plastic. An advantage of using a plastic is that plastics are not corroded by e.g. chloride-containing solutions, acids, hypochlorite etc that are detrimental to stainless steel. Another advantage is that plastics are low density materials that are easy to handle due to the low weight. In a specific embodiment at least one of the porous disks, such as each porous disk, comprises a polyolefin such as polyethylene, polypropylene etc. These materials are readily available at a low cost and can easily be fixed e.g. by welding. If high resistance to very aggressive fluids is desired, the porous disks can be manufactured from fluoropolymers such as polytetrafluoroethylene (PTFE) or from polyetheretherketone (PEEK). These materials also have very low amounts of extractables, allowing for low or zero contamination of the fluid. When polyolefins are used, it is possible to specifically choose a quality releasing a low amount of leachables, such as below 1 mg/l, in the fluid during operation or testing conditions. Where the column is used for separation of biopharmaceuticals, it can also be advantageous to only use materials that are biologically inert, in accordance with United States Pharmacopeia (USP) <88> Class VI.

In one embodiment at least one of the porous disks such as each porous disk comprises a porous sintered plastic material. These materials are prepared by compression moulding of plastic powders and are available both in flat sheet form and as shaped bodies prepared in specifically designed moulds. Two examples of such materials are POREX® (Porex Technologies, Fairburn Ga., USA) and Vyon® (Porvair plc, King's Lynn, UK). They are readily available in pore sizes from about 5 microns to about 100 microns in materials such as polyethylene, polypropylene, ethylene-propylene copolymers, PTFE, polyvinylidene difluoride, ethylene-vinyl acetate copolymers, nylon and polyurethane. For porous retainer disks, pore sizes in the 10-30 micron range can be envisaged, while for porous distributor disks, up to 100 microns or even larger pore sizes can be used.

In one embodiment the solid back plate comprises a plastic. Some advantages of this are the resistance to corrosive aqueous fluids, the low density and the ease of manufacturing by machining or moulding. The back plate can be made from a polyolefin such as polyethylene or polypropylene or from PTFE or PEEK if high resistance to aggressive chemicals is needed. The solid back plate can be made from the same plastic material as the porous disks. This facilitates welding of the porous disks to the plate and minimizes the number of materials used, which can be advantageous from a regulatory point of view.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A fluid distributor for a column, defining a distribution channel of generally conical shape defined by a circular solid back plate with a staircase pattern of at least two internal concentric annular recesses and a packed bed in the column, wherein each annular recess decreases in diameter as the staircase pattern converges towards a tube for inlet and outlet of fluid and wherein the fluid distributor comprises at least two annular fluid-permeable porous disks mounted in said annular recesses.

2. The fluid distributor of claim 1, wherein said annular porous disks fill at least 90% of said annular recesses.

3. The fluid distributor of claim 1, wherein the fluid distributor comprises a porous retainer disk directly facing the packed bed and at least one porous distributor disk filling the part of the distribution channel volume between the porous retainer disk and the solid back plate.

4. The fluid distributor of claim 3, wherein each porous distributor disk has a three-dimensionally connected pore structure.

5. The fluid distributor of claim 1, wherein a first circular or annular porous disk is concentrically fitted inside a second annular porous disk.

6. The fluid distributor of claim 5, wherein said first and second porous disks are planar.

7. The fluid distributor of claim 5, wherein said second porous disk has a lower thickness than said first porous disk.

8. The fluid distributor of claim 5, wherein said second annular porous disk is concentrically fitted inside a third annular porous disk.

9. The fluid distributor of claim 1, wherein a first circular or annular porous disk is mounted in an inner annular recess and a second annular porous disk is mounted in an outer annular recess and concentrically fitted outside said first circular or annular porous disk.

10. The fluid distributor of claim 9, wherein said second annular porous disk has a lower thickness than said first circular or annular porous disk.

11. The fluid distributor of claim 1, wherein a first circular or annular porous disk is mounted in an inner annular recess and a second circular or annular porous disk is mounted in an outer annular recess in planar abutment with said first circular or annular porous disk.

12. The fluid distributor of claim 1, wherein at least one of the porous disks is welded to said solid back plate.

13. The fluid distributor of claim 1, wherein at least one of the porous disks comprises a plastic.

14. The fluid distributor of claim 1, wherein at least one of the porous disks comprises a porous sintered plastic material.

15. The fluid distributor of claim 1, wherein the solid back plate comprises a plastic.

16. The fluid distributor of claim 1, wherein the at least two circular or annular fluid-permeable porous disks are planar.

17. The fluid distributor of claim 1, wherein a first circular or annular porous disk is mounted in an inner annular recess and a second annular porous disk is mounted in an outer annular recess and concentrically fitted outside said first circular or annular porous disk.

18. The fluid distributor of claim 17, wherein said second annular porous disk has a lower thickness than said first circular or annular porous disk.

19. The fluid distributor of claim 1, wherein a first circular or annular fluid-permeable disk is mounted in an inner annular recess and a second circular or annular fluid-permeable porous disk is mounted in an outer annular recess in planar abutment with said first circular or annular porous disk.

20. The fluid distributor of claim 19, wherein a third circular or annular fluid-permeable disk can be mounted in a further outer annular recess in planar abutment with said second circular or annular porous disk.

* * * * *